(12) United States Patent
Wildgoose (10) Patent No.: US 9,881,782 B2
(45) Date of Patent: Jan. 30, 2018

(54) METHOD FOR SEPARATING IONS ACCORDING TO A PHYSICOCHEMICAL PROPERTY

(71) Applicant: Micromass UK Limited, Wilmslow (GB)

(72) Inventor: Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/125,396

(22) PCT Filed: Mar. 10, 2015

(86) PCT No.: PCT/GB2015/050695
§ 371 (c)(1),
(2) Date: Sep. 12, 2016

(87) PCT Pub. No.: WO2015/136266
PCT Pub. Date: Sep. 17, 2015

(65) Prior Publication Data
US 2017/0213716 A1 Jul. 27, 2017

(30) Foreign Application Priority Data

Mar. 10, 2014 (EP) ..................................... 14158598
Mar. 10, 2014 (GB) ..................................... 1404177.6

(51) Int. Cl.
*H01J 49/06* (2006.01)
*G01N 27/62* (2006.01)
*H01J 49/42* (2006.01)
*H01J 49/40* (2006.01)

(52) U.S. Cl.
CPC .......... *H01J 49/427* (2013.01); *G01N 27/622* (2013.01); *H01J 49/062* (2013.01); *H01J 49/408* (2013.01)

(58) Field of Classification Search
CPC ...... H01J 49/427; H01J 49/062; H01J 49/408; G01N 27/622
USPC ................................ 250/281, 282, 283, 290
See application file for complete search history.

(56) References Cited

U.S. PATENT DOCUMENTS

| 7,211,792 | B2 | 5/2007 | Yamaguchi et al. |
| 7,932,487 | B2 | 4/2011 | Kovtoun et al. |
| 8,093,555 | B2 | 1/2012 | Yamaguchi |
| 8,164,054 | B2 | 4/2012 | Nishiguchi et al. |
| 8,263,932 | B2 | 9/2012 | Yamaguchi |
| 9,207,206 | B2 | 12/2015 | Makarov |
| 9,281,172 | B2 | 3/2016 | Bateman et al. |

(Continued)

*Primary Examiner* — Nicole Ippolito (57) ABSTRACT

A method of separating ions according to a physicochemical property is disclosed. The method comprises causing ions to perform a plurality of cycles along or around an ion guiding path such that the ions separate according to said physicochemical property. The ions are ejected from an ion exit region by applying a force to the ions such that only having a physicochemical property value that is either above or below a threshold value are ejected as they pass through the exit region, but ions having a physicochemical property value either below or above said threshold value, respectively, remain within the ion guiding path. The force applied to the ions within the exit region is varied with time such that the physicochemical property value of the ions ejected from the ion guiding region varies with time.

20 Claims, 1 Drawing Sheet (56) References Cited

U.S. PATENT DOCUMENTS

| | | | |
|---|---|---|---|
| 9,412,575 B2 | 8/2016 | Green et al. | |
| 2007/0034810 A1* | 2/2007 | Hoyes | H01J 49/427 |
| | | | 250/396 R |
| 2007/0278397 A1* | 12/2007 | Bateman | G01N 27/622 |
| | | | 250/286 |
| 2010/0084549 A1* | 4/2010 | Ermakov | H01J 49/4245 |
| | | | 250/283 |
| 2012/0112060 A1 | 5/2012 | Kinugawa et al. | |
| 2014/0312222 A1 | 10/2014 | Giles et al. | |
| 2014/0353487 A1* | 12/2014 | Giles | G01N 27/622 |
| | | | 250/282 |

\* cited by examiner

METHOD FOR SEPARATING IONS ACCORDING TO A PHYSICOCHEMICAL PROPERTY

CROSS REFERENCE TO RELATED APPLICATION APPLICATIONS

This application is the National Stage of International Application No. PCT/GB2015/050695, filed 10 Mar. 2015 which claims priority from and the benefit of United Kingdom patent application No. 1404177.6 filed on 10 Mar. 2014 and European patent application No. 14158598.4 filed on 10 Mar. 2014. The entire contents of these applications are incorporated herein by reference.

BACKGROUND TO THE PRESENT INVENTION

The present invention relates to a method and device for separating ions according to a physicochemical property, such as ion mobility or mass to charge ratio.

A conventional ion mobility spectrometer or separator ("IMS") employs a static potential gradient to drive ions along a drift tube such that the ions separate according to their ion mobility as they pass along the drift tube. It is well established that increasing the length of the drift tube can lead to improved resolution or resolving power of the device. This is also true for IMS devices that employ a travelling DC potential, rather than a static potential gradient, to drive the ions along the drift tube. Such a device employing a DC travelling potential has the advantage that there is no requirement for a DC field along the whole length of the drift tube. This enables the entrance of the IMS device to be at the same DC potential as the exit of the device.

WO 2007/066114 discloses an IMS device that exploits the above-mentioned benefit by configuring the drift tube as a closed loop configuration, which enables the drift length of the device to be increased by causing ions to perform multiple passes around the closed loop drift region. Whilst this technique enables the effective length of the drift region to be increased significantly, a problem arises when the ions are to be ejected from the device for further analysis. More specifically, at any given position within the device ions of different mobilities will have undergone a different number of cycles around the closed loop drift region. This leads to the resolution of the device being ion mobility dependent, which is undesirable.

WO 2013/093515 discloses a device wherein ions are separated according to their ion mobility as they pass down a DC potential gradient arranged around a closed-loop drift region. The DC potential gradient moves around the drift region with time, along with an exit region, such that ions are ejected from the drift region as they reach the lower end of the DC potential gradient. Although this technique offers advantages, it may be complicated to implement, as it requires the exit region to move around the device. Furthermore, ions of different ion mobilities travel different lengths around the drift region before being ejected and so the resolution of the device is ion mobility dependent.

WO 2013/093513 also discloses a device wherein ions are separated according to their ion mobility as they pass down a DC potential gradient arranged around a closed-loop drift region. The device is configured to ensure that higher mobility ions do not pass around the closed-loop ion guide and remix with the lower mobility ions by restricting the drift length of the experiment. Although this technique offers advantages, it may provide a relatively low resolution as it restricts the number of cycles of the ions around the closed loop drift region.

It is desired to provide an improved method of separating ions according to a physicochemical property.

SUMMARY OF THE PRESENT INVENTION

The present invention provides a method of separating ions according to a physicochemical property comprising:

providing an ion guide having a plurality of electrodes arranged to form an ion guiding path;

causing said ions to perform a plurality of cycles along or around said ion guiding path such that said ions separate according to said physicochemical property as they pass along or around said ion guiding path;

ejecting ions from an ion exit region of said ion guiding path by applying a force to the ions in said exit region such that only ions in the exit region having a physicochemical property value that is either above or below a threshold value are ejected from the ion guiding path as they pass through said exit region, and ions in said exit region having a physicochemical property value either below or above said threshold value, respectively, remain within the ion guiding path; and varying said force applied to ions within the exit region with time such that said threshold value varies with time and hence the physicochemical property value of the ions ejected from the ion guiding region varies with time.

The present invention enables ions to be selectively ejected from the exit region of the ion guiding path according to their physicochemical property values, even when ions of different physicochemical property values pass through the exit region simultaneously. This enables one to select the number of cycles along or around the ion guiding region that ions of any given physicochemical property value undertake. In a particularly preferred method of the present invention, this may be used to ensure that ions of different physicochemical property values undergo the same number of cycles along or around the ion guiding path before being ejected from the ion guiding path. This may ensure that the resolution of the ion separation device is independent of the physicochemical property values of the ions.

The present invention is in contrast to known arrangements, such as those of WO 2013/093515 and WO 2013/093513 described above, in that the ion exit region in known arrangements ejects all ions that are within the exit region simultaneously, regardless of their physicochemical property values. Such known devices are therefore unable to selectively allow only ions of desired physicochemical property value(s) to leave the ion guiding region when ions of different physicochemical property values pass through the exit region simultaneously.

GB 2499587 discloses an ion mobility separator in which ions make multiple passes along a separation region that is arranged between two ion mirrors. Ions may be extracted from the separator by temporarily switching off an ion mirror. However, this document does not disclose ejecting ions above (or below) a threshold physicochemical property value from an exit region, whilst retaining ions below (or above) the threshold physicochemical property value in the exit region. Also, GB '587 does not disclose varying the force applied to the ions in the exit region so that the threshold value for the ejected ions varies with time. Rather, the ion mirror is simply switched off when the ions desired to be ejected are in the mirror region (i.e. exit region).

Accordingly, this prior art method cannot provide the advantages of the present invention.

US 2009/0179150 discloses a loop ion guide comprising first and second mass filters 124,140 and first and second fragmentation cells 128,151; see FIG. 1. Ions may be diverted out of the loop path at switching device 144 and onto detector 150. However, the ions do not separate according to physicochemical property as they pass around the loop. Also, the force applied to the ions at the exit region is not varied with time such that the threshold value of the ions that are ejected is varied with time. As such, this prior art method cannot provide the advantages of the present invention.

The method may comprise calculating or experimentally determining the different times taken for ions having a plurality of different values of said physicochemical property to travel from an ion entrance region of said ion guiding path to said ion exit region whilst having completed said plurality of cycles along or around the ion guiding path therebetween; and then injecting ions having said plurality of different values of said physicochemical property into said ion guiding region at said ion injection region; and then performing the method of claim 1, wherein the ion ejection from said exit region is controlled based on said calculated or determined times of travel so as to eject said ions having said plurality of different values of said physicochemical property after each of the ions has performed said plurality of cycles along or around the ion guiding region.

Preferably, said ions that remain within the ion guiding path are caused to perform at least another cycle along or around the ion guiding path before being ejected from the ion guiding path, preferably at said exit region.

Preferably, said step of applying a force to the ions in said exit region comprises: allowing or forcing said ions to pass through the exit region in a first direction with different speeds that depend on said physicochemical property values, and providing a force on these ions in a second different direction such that ions having a speed in the first direction that is either above or below a threshold speed are forced or travel along a first pathway and exit the ion guiding region, whereas ions having a speed in the first direction that is either below or above the threshold speed, respectively, are forced or travel along a second pathway that retains these ions within the ion guiding path. Alternatively, or additionally, said step of applying a force to the ions in said exit region may comprise: allowing or forcing said ions to separate in a first direction according to said physicochemical property values as they pass through the exit region, and providing a force on these ions in a second different direction such that ions having said physicochemical property value that is either above or below a threshold value are forced or travel along a first pathway and exit the ion guiding region, whereas ions having a physicochemical property value either below or above said threshold value, respectively, are forced or travel along a second pathway that retains these ions within the ion guiding path.

Said first and second directions are preferably substantially orthogonal to each other.

Preferably, said step of causing ions to separate in said first direction comprises applying one of the following in said first direction: a DC potential gradient; a gas flow; a voltage pulse; or a pseudo-potential force from an RF potential.

The step of providing a force in said second direction may comprise applying one of the following in said second direction: a single or repeating DC travelling wave that travels along the exit region in the second direction; a gas flow; a DC potential gradient; a voltage pulse; or a pseudo-potential force from an RF potential.

The force on the ions in the second different direction is preferably independent of said physicochemical property values of the ions.

The force applied to ions in the exit region is preferably varied with time such that all ions, or ions having a predetermined range of physicochemical property values, are ejected from the ion guiding region only after having performed a predetermined number of cycles along or around the ion guiding path or after having traveled the same distance along or around said ion guiding region, and preferably no more than said predetermined number of cycles along or around the ion guiding path. Alternatively, the operation of the exit region may be synchronised with the motion of the ions around or along the ion guiding region such that ions having different values of said physicochemical property value, or all ions, are ejected from the ion guiding region at said exit region after having performed the same number of cycles along or around the ion guiding region, or after having traveled the same distance along or around said ion guiding region.

The ion guiding path is preferably a closed-loop, circular, oval or elliptical ion guiding path.

Alternatively, the ion guiding path may be a substantially linear or open-ended ion guiding path, and the method may further comprise reflecting the ions between two ends of said linear or open-ended ion guiding path such that the ions perform said plurality of cycles along the ion guiding region.

The method may comprise simultaneously pulsing ions having a plurality of different values of said physicochemical property into said ion guiding region.

The method preferably comprises injecting ions and/or ejecting ions from said ion guiding path in a direction tangential to said on guiding path.

Preferably, said physicochemical property is ion mobility, and said ion guiding region is preferably a drift region in which ions separate according to their ion mobility.

Alternatively, said physicochemical property may be mass to charge ratio, and said ion guiding region may be a time of flight region in which ions separate according to their mass to charge ratio.

The step of applying a force to the ions in said exit region may cause ions in the exit region having values of said physicochemical property between an upper threshold value and a lower threshold value to be ejected from the ion guiding path as they pass through said exit region and ions in said exit region having values of said physicochemical property below said lower threshold and above said upper threshold to remain within the ion guiding path. The method may comprise varying said force applied to ions in the exit region with time such that said lower and/or upper threshold values vary with time and hence the band of physicochemical property values of the ions ejected from the ion guiding region varies with time.

The method may comprise allowing or forcing ions having different values of said physicochemical property to travel along or around said ion guiding region at different speeds such that they separate from each other as they travel, wherein ions travelling at a higher speed overlap, overtake or remix within ions travelling at a lower speed as the ions perform said plurality of cycles along or around said ion guiding path; wherein the ions overlap, overtake or remix at least at said exit region.

The method preferably comprises providing said ion guiding region comprising a plurality of electrodes spaced along the axial length of the ion guiding region, wherein one or more DC potentials are applied to said electrodes so as to drive said ions along or around the ion guiding region.

The method preferably comprises applying one or more DC potentials or DC potential waves to successive ones of said electrodes with time such that said ions are driven along or around said ion guiding region. Alternatively, and less preferably, the method may comprise providing a potential difference along at least a portion of the axial length of said ion guiding region so as to drive ions along or around said ion guiding region.

Some methods may comprise providing the ion guiding region as a time of flight region having substantially no electric field in the axial direction of the ion guiding region. For example, when said physicochemical property is mass to charge ratio the ion guiding region may be a time of flight region having no electric field along its longitudinal axis.

The method preferably comprises applying RF voltages to electrodes of said ion guiding region so as to radially confine ions to the longitudinal axis of said ion guiding region.

The method may comprise varying the number of cycles that ions perform along or around said ion guiding region before being ejected from said ion exit region.

As described herein, the physicochemical property values of the ions that are ejected at the exit region vary as a function of time. It is contemplated that the exit region may be adjusted in a continuous manner so as to perform this function or may be adjusted in a stepped manner so as to perform this function.

The present invention also provides a method of filtering ions according to a physicochemical property, wherein the method comprises any one of the methods of separating ions described herein, and wherein ions of a desired value or range of desired values of said physicochemical property are preferably stored in said ion guiding region or are ejected from said ion guiding region.

The present invention also provides a method of ion mobility spectrometry and/or mass spectrometry comprising any one of the methods described herein.

The method of spectrometry preferably comprises detecting and/or mass analysing and/or ion mobility analysing ions ejected from said ion guiding path.

The present invention also provides a device for separating ions according to a physicochemical property comprising:

an ion guide having a plurality of electrodes arranged to form an ion guiding path;

a device for applying a force to the ions within an ion exit region of said ion guiding path; and a controller arranged and adapted to:

(i) cause said ions to perform a plurality of cycles along or around said ion guiding path such that said ions separate according to said physicochemical property as they pass along or around said ion guiding path;

(ii) eject ions from said ion exit region of said ion guiding path by applying a force to the ions in said exit region such that only ions in the exit region having a physicochemical property value that is either above or below a threshold value are ejected from the ion guiding path as they pass through said exit region, and ions in said exit region having a physicochemical property value either below or above said threshold value, respectively, remain within the ion guiding path; and (iii) vary said force applied to ions within the exit region with time such that said threshold value varies with time and hence the physicochemical property value of the ions ejected from the ion guiding region varies with time.

The device may be arranged and configured to perform any one of the methods described herein.

The present invention also provides a physicochemical property filter comprising a device described herein, wherein said filter is preferably arranged and configured so as to store or eject ions of a desired value or desired range of physicochemical property values from the ion guiding region.

The present invention also provides a mass and/or ion mobility spectrometer comprising a device or filter as described herein.

The spectrometer preferably comprises a detector and/or mass analyser and/or ion mobility analyser for detecting and/or analysing ions ejected from said ion guiding path.

The spectrometer disclosed herein may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an on-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform ion Cyclotron Resonance ("FTICR") mass analyser, (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser, (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may optionally comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

Figure 1:
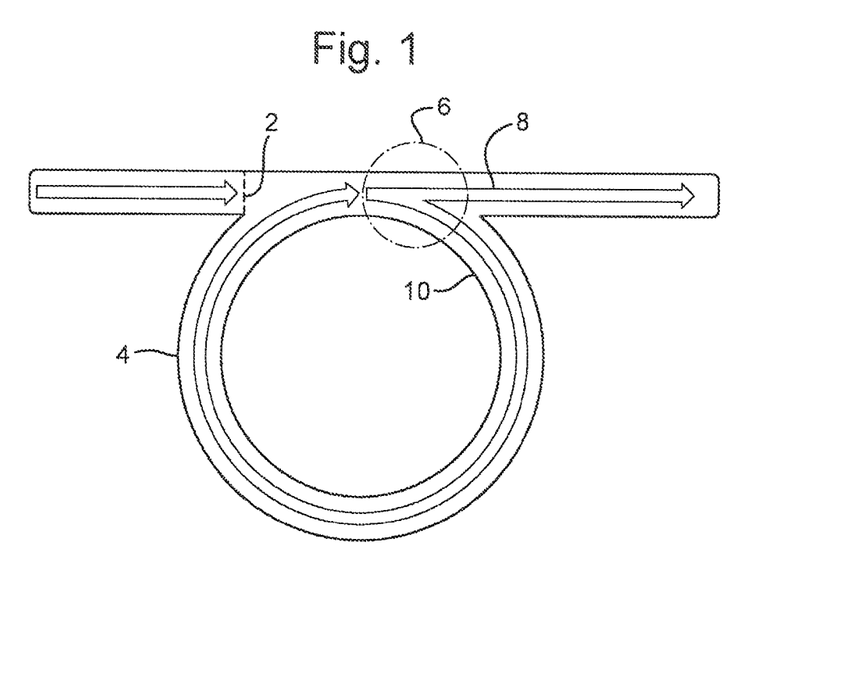
FIG. 1 shows a preferred embodiment of a device for separating ions according to their ion mobilities in a closed-loop ion guiding region, wherein the device comprises an exit region that selectively ejects ions from the ion guiding region when the ions have performed a preset number of cycles around the device.

FIG. 1 shows a schematic of an ion mobility separator (IMS) device according to a preferred embodiment of the present invention. The IMS device comprises an ion entrance gate 2 for allowing ions into the IMS device, a closed-loop IMS drift region 4 and an exit region 6 for causing ions to exit the IMS drift region 4. The IMS device is comprised of a plurality of electrodes that confine ions such that they travel along the axial length of the device. The electrodes are preferably separated along the axis of the device such that different electrical potentials can be applied to different axial regions of the device. During operation, the entrance gate 2 simultaneously pulses ions of different ion mobilities into the closed-loop drift region 4. RF potentials are applied to the electrodes of the device so as to radially confine ions at the longitudinal axis of the device. One or more DC potentials are preferably applied successively to the axially separated electrodes around the closed-loop drift region 4 so as to drive the ions around the drift region 4. The drift region 4 is filled with a background gas, which causes the ions to separate according to their ion mobility as they are driven around the drift region 4. Ions with high ion mobility travel around the closed-loop drift region 4 at a higher speed than ions with lower ion mobility. As the drift region 4 is a closed-loop drift region the ions with high ion mobility eventually catch up with and lap the ions with lower ion mobility.

According to a preferred embodiment, it is only desired to extract ions from the closed-loop drift region 4 after the ions have performed a desired number of cycles around the drift region 4. This is achieved by controlling the electric fields in the exit region 6 such that ions may only exit the closed-loop drift region 4 after they have performed a predetermined number of cycles around the drift region 4. More specifically, the exit region 6 preferably only allows ions above a certain minimum ion mobility to exit the drift region 6 at any given time and the value of this minimum on mobility is varied with time such that an ion of any given ion mobility may only exit the drift region 4 after performing a predetermined number of cycles around the drift region 4.

By way of example, ions having a first, high ion mobility undergo a predetermined number of cycles around the drift region 4 relatively quickly and then arrive at the exit region 6 at a first time. At this first time, the field in the exit region 6 is set so as to only allow ions having an ion mobility at or above said first ion mobility to exit the drift region 4. All other ions are not allowed to exit the drift region 4 and so ions having lower ion mobility continue around the drift region 4. Ions having a second, lower ion mobility undergo said predetermined number of cycles around the drift region 4 relatively slowly and then arrive at the exit region 6 at a second time that is later than the first time. At this second time, the field in the exit region 4 is set so as to only allow ions having an ion mobility at or above said second ion mobility to exit the drift region 4. As the ion mobility of the ions that are allowed to exit the exit region 6 varies as a function of time, this enables the device to ensure that ions of different ion mobilities perform the same number of predetermined cycles around the drift region 4 before being ejected and hence ensures that all ions are subjected to the same drift length in the IMS device.

In practice, the relationship between drift time around the drift region 4, position of the ions and ion mobility can be determined from fundamental calculations, simulations or calibration. This allows calculation of the ion mobility ranges that will be present at the exit region 6 as a function of time and so can be used to determine how to control the extraction field in the exit region 6 so as to extract ions from the drift region 4 only after they have performed a predetermined number of cycles around the drift region 4.

By way of example, it can be shown that the time $T_i$ for an ion having an ion mobility $K_i$ to perform N cycles around a closed-loop drift region is $T_i=(A \times N \times C)/K_i^p$; where C is the length of one cycle around the drift region, A is a calibration constant related to the force that drives the ions around the closed-loop, such as travelling wave parameters, volts etc., and p is the term in the power law relationship that relates to the time-averaged driving force for driving ions around the closed-loop. A value of p=1 may be used for drift tubes having a static DC potential for driving ions around the device. A value of p=2, for example, may be used for drift tubes having a DC travelling wave for driving ions around the device.

If the extraction field at the exit region 6 is scanned with time so that at time $T_i$ ions at or above ion mobility $K_i$ are deflected out of the drift region 4, whereas ions below $K_i$ are retained within the drift region 4 then all ions, irrespective of their ion mobility, will undergo N and only N cycles around the closed loop drift region 4 before being ejected.

As described above, the exit region 6 is required to spatially separate and eject ions according to their mobility. In the example wherein only ions having an ion mobility at or above a certain minimum value are allowed to exit the exit region 6 at any given time, the resolution requirement for filtering ions out of the drift region 4 at the exit region 6 can be shown to be R=p×N. This is because the device is only required to separate ions that have undergone N cycles around the drift region 4 from ions that have undergone N−1 cycles around the drift region 4.

Figure 2:
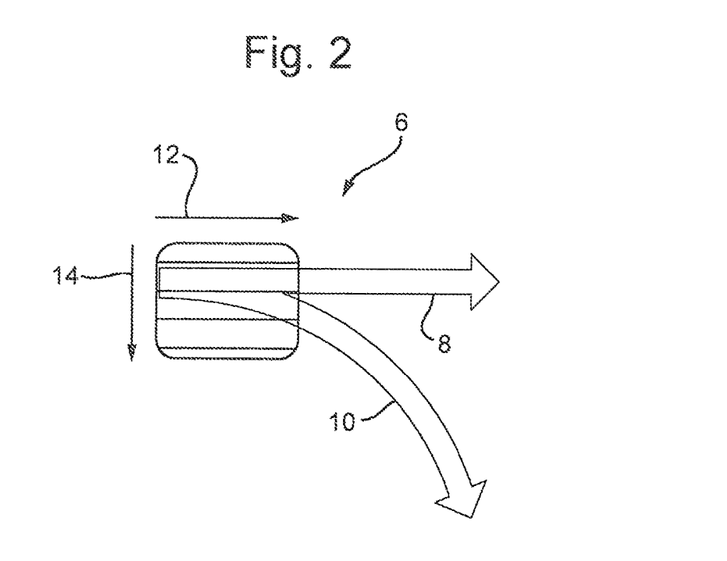
FIG. 2 shows a schematic of an embodiment of the exit region of the device in FIG. 1.

FIG. 2 shows an embodiment of the exit region 6 of the device in FIG. 1. As described above, the exit region 6 causes ions to be ejected from the drift region 4 as a function of their ion mobility. The exit region 6 is arranged within the closed-loop drift region 4 such that ions pass through the exit region 6 as they cycle around the drift region 4. Ions enter the exit region 6 and each ion is then directed along one of two pathways, depending upon its ion mobility. Ions having an ion mobility at or above a certain minimum value are directed along a first pathway 8 that ejects the ions from the drift region 4. Ions having an ion mobility below the certain minimum value are directed along a second pathway 10 that retains the ions within the drift region 4 so that they continue to make another cycle around the drift region 4.

In order to direct the ions along different pathways depending upon their ion mobilities, a static DC field 12 may be arranged in a first direction along the exit region 6 and a DC travelling wave 14 may be caused to repeatedly travel in a second direction along the exit region 6. The first and second directions are preferably orthogonal. The static DC field 12 causes ions to travel in the first direction with velocities that are dependent upon the ion mobilities of the ions. This causes the ions to separate in the first direction as a function of their ion mobilities, i.e. ions of higher ion mobilities travel faster in the first direction than ions of lower ion mobilities. The DC travelling wave 14 causes ions to travel in the second direction with substantially the same average velocity, irrespective of their ion mobilities. The static DC field 12 causes ions having ion mobilities above the certain minimum value to traverse the exit region 6 relatively quickly and to leave the exit region 6 along the first pathway 8, before the travelling DC wave 14 is able to force these ions in the second direction to a degree that would cause them to leave the exit region 6 along the second pathway 10. As such, these ions travel along the first pathway 8 and are ejected from the drift region 4 as they pass through the exit region 6. On the other hand, the static DC field causes ions having ion mobilities below the certain minimum value travel to travel through the exit region 6 relatively slowly in the first direction. The DC travelling wave 14 moves at a rate that is sufficient to force these ions in the second direction to a degree that is sufficient to cause these ions to leave the exit region 6 along the second pathway 10. As such, these ions are forced to continue around the drift region 4 for at least another cycle.

The static DC field 12 and/or DC travelling wave 14 are altered with time such that said certain minimum value of ion mobility varies with time and such that ions of all ion mobilities only perform the same number of cycles around the drift region 4 before being ejected. For example, the magnitude of the static DC field 12 may be varied with time. Alternatively, or additionally, the amplitude and/or speed of the DC travelling wave 14 may be varied with time so as to achieve the above effect. In practice, the ion mobility peak width would need to be taken into account when determining the scan function with time at the exit region 6.

Although the present invention has been described with reference to preferred embodiments, it will be understood by those skilled in the art that various changes in form and detail may be made without departing from the scope of the invention as set forth in the accompanying claims.

For example, alternative methods of ejecting ions from the exit region 6 as a function of their ion mobilities are also envisioned. For example, a differential mobility analyser ("DMA") method may be used wherein a gas flow is used to cause the ions to travel along the first or second pathway 8,10 depending upon their ion mobilities. For example, a gas flow in the second direction may replace the DC travelling wave 14 in the above-described embodiment.

The ion ejection at the exit region 6 may be based on a physicochemical property of the ions that is correlated to ion mobility, such as mass to charge ratio, and particularly by use of time of flight mass to charge ratio separation in the exit region 6.

The exit region 6 may be based on a temporal separation that uses a faster, lower resolution nested IMS, wherein multiple fast IMS cycles are completed per closed loop IMS peak. This relates to a system where the exit region 6 can do very fast pulsed IMS separations. This allows many fast IMS separations per experiment, wherein in each of these separations one can choose the IMS regions to be ejected or maintained within the ion guiding region.

The device can be scanned such that the number of cycles around the drift region 4 that the ions perform before being ejected is varied.

As described above, the ion mobilities of the ions that are ejected at the exit region 6 varies as a function of time. It is contemplated that the exit region 6 may be adjusted in a continuous manner so as to perform this function or may be adjusted in a stepped manner so as to perform this function.

The above embodiments have been described wherein the exit region 6 operates as a high pass filter so as to eject ions having an ion mobility above a threshold value at any given time. However, it is contemplated that the exit region 6 may alternatively operate in a band pass mode such that only ions having ion mobilities between an upper and lower threshold are ejected at the exit region 6 at any given time. The upper and lower thresholds would be varied as a function of time such that the ion mobility bend ejected varies as a function of time. Less preferably, the device may operate as a low pass filter to eject ions having an ion mobility below a threshold value at any given time, wherein the threshold varies with time.

Analytical devices, such as a mass to charge ratio filter, may be present within the drift region 4.

Ion filtering devices may be provided in the drift region 4.

It is recognised that the device described herein may be operated as a filter, with only a restricted range of ion mobilities being stored or ejected.

Although a closed-loop drift region 4 has been described, other non-closed loop drift regions 4 may also be used. For example, ions may be repeatedly reflected back and forth along drift region 4 that is not closed-looped and which may be, for example, a linear drift region 4.

The ions may be confined within the drift region 4 by constructing the drift region 4 from any one or combination of the following: multipole rod sets; quadrupoles; hexapoles; octopoles; ion tunnel ion guides; ion funnel ion guides; and sandwich plate ion guides. RF and/or DC potentials may be applied to these ion guides so as to confine the ions within the drift region.

It is preferred that one or more DC travelling potential or wave is used to drive ions around or along the drift region 4. However, it is also contemplated that methods other than travelling waves may be used to drive the ions along the drift region 4, such as axial/tangential electric or magnetic fields.

The ion entrance 2 and/or ion exit 6 of the drift region 4 is preferably tangential to the drift region 4. However, the ion entrance 2 and/or ion exit 6 may be non-tangential. The ion entrance 2 and/or ion exit 6 may be coaxial with each other such that ions enter and exit the drift region 4 along the same axis. Alternatively, the ion entrance axis may be different to the ion exit axis.

The drift region 4 is preferably a closed-loop drift region. The drift region 4 may be substantially circular, elliptical, oval or any other shape. The drift region 4 is preferably progressively curved, although in less preferred embodiments it may change direction along its axial length at sharp angles such as right angles.

The ion entrance point 2 and the ion exit point 6 may be at the same point on the drift region 4 or at different points.

The drift region 4 may be provided with ion entrances 2 and/or exit regions 6 of the type described herein.

A wide range of ionisation sources, fragmentation devices or analysers may be provided upstream and/or downstream of the drift region 4.

Ions that are ejected from the exit region 6 may be reinjected into the drift region 4 such that they travel in the opposite direction to that which they were travelling when the exited the drift region 4.

It is also contemplated that multiple IMS devices described herein may be coupled together such that ions ejected from one IMS device are injected into another of the IMS devices. Multiple IMS devices may be combined in series and/or in parallel.

It is contemplated that one or more DC travelling wave may drive the ions along or around the drift region 4 and that the speed of the one or more wave may vary or may even stop within the drift cycle. For example, the speed may vary or stop within the cycle time around a closed-loop drift region 4.

Although the preferred embodiments have been described in relation to ion mobility separators and drift regions, it is contemplated that the present invention may separate and eject ions according to physicochemical properties other than ion mobility. For example, ions may be separated by mass to charge ratio in a time of flight region, rather than being separated by ion mobility in a drift region. Corresponding features to those described above in relation to the IMS device may be provided for the mass to charge ratio based device. For example, the exit region may eject ions having mass to charge ratios at or above a certain minimum value at any given time (or within a certain band) and said minimum value (or band) may vary with time. The time of flight region may be a closed-loop region or may be a non-closed loop region, e.g. a linear device, wherein ions are repeatedly reflected back and forth along the device.

The invention claimed is:

1. A method of separating ions according to a physicochemical property comprising:

providing an ion guide having a plurality of electrodes arranged to form an ion guiding path;

causing said ions to perform a plurality of cycles along or around said ion guiding path such that said ions separate according to said physicochemical property as they pass along or around said ion guiding path;

ejecting ions from an ion exit region of said ion guiding path by applying a force to the ions in said exit region such that only ions in the exit region having a physicochemical property value that is either above or below a threshold value are ejected from the ion guiding path as they pass through said exit region, and ions in said exit region having a physicochemical property value either below or above said threshold value, respectively, remain within the ion guiding path; and varying said force applied to ions within the exit region with time such that said threshold value varies with time and hence the physicochemical property value of the ions ejected from the ion guiding region varies with time.

2. The method of claim 1, comprising calculating or experimentally determining the different times taken for ions having a plurality of different values of said physicochemical property to travel from an ion entrance region of said ion guiding path to said ion exit region whilst having completed said plurality of cycles along or around the ion guiding path therebetween; and then injecting ions having said plurality of different values of said physicochemical property into said ion guiding region at said ion injection region; and then performing the method of claim 1, wherein the ion ejection from said exit region is controlled based on said calculated or determined times of travel so as to eject said ions having said plurality of different values of said physicochemical property after each of the ions has performed said plurality of cycles along or around the ion guiding region.

3. The method of claim 1, wherein said ions that remain within the ion guiding path are caused to perform at least another cycle along or around the ion guiding path before being ejected from the ion guiding path, preferably at said exit region.

4. The method of claim 1, wherein said step of applying a force to the ions in said exit region comprises: allowing or forcing said ions to pass through the exit region in a first direction with different speeds that depend on said physicochemical property values, and providing a force on these ions in a second different direction such that ions having a speed in the first direction that is either above or below a threshold speed are forced or travel along a first pathway and exit the ion guiding region, whereas ions having a speed in the first direction that is either below or above the threshold speed, respectively, are forced or travel along a second pathway that retains these ions within the ion guiding path; and/or wherein said step of applying a force to the ions in said exit region comprises: allowing or forcing said ions to separate in a first direction according to said physicochemical property values as they pass through the exit region, and providing a force on these ions in a second different direction such that ions having said physicochemical property value that is either above or below a threshold value are forced or travel along a first pathway and exit the ion guiding region, whereas ions having a physicochemical property value either below or above said threshold value, respectively, are forced or travel along a second pathway that retains these ions within the ion guiding path.

5. The method of claim 4, wherein said step of causing ions to separate in said first direction comprises applying one of the following in said first direction: a DC potential gradient; a gas flow; a voltage pulse; or a pseudo-potential force from an RF potential.

6. The method of claim 4, wherein said step of providing a force in said second direction comprises applying one of the following in said second direction: a single or repeating DC travelling wave that travels along the exit region in the second direction; a gas flow; a DC potential gradient; a voltage pulse; or a pseudo-potential force from an RF potential.

7. The method of claim 4, wherein said force on the ions in the second different direction is independent of said physicochemical property values of the ions.

8. The method of claim 1, wherein said force applied to ions in the exit region is varied with time such that all ions, or ions having a predetermined range of physicochemical property values, are ejected from the ion guiding region only after having performed a predetermined number of cycles along or around the ion guiding path or after having travelled the same distance along or around said ion guiding region, and preferably no more than said predetermined number of cycles along or around the ion guiding path; or wherein the operation of the exit region is synchronised with the motion of the ions around or along the ion guiding region such that ions having different values of said physicochemical property value, or all ions, are ejected from the ion guiding region at said exit region after having performed the same number of cycles along or around the ion guiding region, or after having travelled the same distance along or around said ion guiding region.

9. The method of claim 1, wherein said ion guiding path is a closed-loop, circular, oval or elliptical ion guiding path.

10. The method of claim 1, wherein said ion guiding path is a substantially linear or open-ended ion guiding path, the method preferably further comprising reflecting the ions between two ends of said linear or open-ended ion guiding path such that the ions perform said plurality of cycles along the ion guiding region.

11. The method of claim 1, comprising simultaneously pulsing ions having a plurality of different values of said physicochemical property into said ion guiding region.

12. The method of claim 1, wherein said physicochemical property is ion mobility, and wherein said ion guiding region is preferably a drift region in which ions separate according to their ion mobility.

13. The method of claim 1, wherein said physicochemical property is mass to charge ratio, and wherein said ion guiding region is preferably a time of flight region in which ions separate according to their mass to charge ratio.

14. The method of claim 1, wherein said step of applying a force to the ions in said exit region causes ions in the exit region having values of said physicochemical property between an upper threshold value and a lower threshold value to be ejected from the ion guiding path as they pass through said exit region and ions in said exit region having values of said physicochemical property below said lower threshold and above said upper threshold to remain within the ion guiding path, the method comprising varying said force applied to ions in the exit region with time such that said lower and/or upper threshold values vary with time and hence the band of physicochemical property values of the ions ejected from the ion guiding region varies with time.

15. The method of claim 1, comprising allowing or forcing ions having different values of said physicochemical property to travel along or around said ion guiding region at different speeds such that they separate from each other as they travel, wherein ions travelling at a higher speed overlap, overtake or remix within ions travelling at a lower speed as the ions perform said plurality of cycles along or around said ion guiding path; wherein the ions overlap, overtake or remix at least at said exit region.

16. A method of filtering ions according to a physicochemical property, said method comprising performing the method of claim 1, wherein ions of a desired value or range of desired values of said physicochemical property are preferably stored in said ion guiding region or are ejected from said ion guiding region.

17. A method of ion mobility spectrometry and/or mass spectrometry comprising a method as claimed in claim 1.

18. A device for separating ions according to a physicochemical property comprising:
   an ion guide having a plurality of electrodes arranged to form an ion guiding path;
   a device for applying a force to the ions within an ion exit region of said ion guiding path; and
   a controller arranged and adapted to:
   (i) cause said ions to perform a plurality of cycles along or around said ion guiding path such that said ions separate according to said physicochemical property as they pass along or around said ion guiding path;
   (ii) eject ions from said ion exit region of said ion guiding path by applying a force to the ions in said exit region such that only ions in the exit region having a physicochemical property value that is either above or below a threshold value are ejected from the ion guiding path as they pass through said exit region, and ions in said exit region having a physicochemical property value either below or above said threshold value, respectively, remain within the ion guiding path; and
   (iii) vary said force applied to ions within the exit region with time such that said threshold value varies with time and hence the physicochemical property value of the ions ejected from the ion guiding region varies with time.

19. A physicochemical property filter comprising a device as claimed in claim 18, wherein said filter is preferably arranged and configured so as to store or eject ions of a desired value or desired range of physicochemical property values from the ion guiding region.

20. A mass and/or ion mobility spectrometer comprising a device or filter as claimed in claim 18.

* * * * *